United States Patent [19]

Mahn et al.

[11] Patent Number: 4,725,611
[45] Date of Patent: Feb. 16, 1988

[54] SYNERGISTIC MICROBIOCIDAL COMPOSITIONS CONTAINING A MIXTURE OF A BICYCLICPOLYOXYMETHYLENEOX-AZOLIDINE AND A 4-ISOTHIAZOLIN-3-ONE

[75] Inventors: Frederick R. Mahn, Verona; Lora J. Bogdany, Denville; Joseph J. Baron, Morris Plains; Edward G. Knapick; Edward M. Antonucci, both of Randolph, all of N.J.

[73] Assignee: Drew Chemical Corporation, Boonton, N.J.

[21] Appl. No.: 75,908

[22] Filed: Jul. 20, 1987

Related U.S. Application Data

[63] Continuation-in-part of Ser. No. 894,264, Aug. 6, 1986, abandoned.

[51] Int. Cl.$^4$ .................. A01N 43/76; A01N 43/80
[52] U.S. Cl. ............................ 514/372; 514/375
[58] Field of Search ........................... 514/372, 375

[56] References Cited

U.S. PATENT DOCUMENTS 4,135,945  1/1979  Buono et al. ............... 106/308 N
4,173,643  11/1979  Law ........................... 514/372

Primary Examiner—Allen J. Robinson
Attorney, Agent, or Firm—Walter H. Schneider

[57] ABSTRACT

A synergistic microbiocidal composition comprising as Component (1) a 4-isothiazolin-3-one and as Component (2) a bicyclic polyoxymethyleneoxazolidine of the formula:

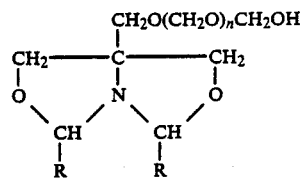

in which each R represents hydrogen, an alkyl of 1–6 carbons, phenyl, halophenyl or —$(CH_2O)_mCH_2OH$ in which m is 0–2 and n is 0–4; Component 1/Component 2 being in a weight ratio of at least 1:1.

2 Claims, No Drawings

SYNERGISTIC MICROBIOCIDAL COMPOSITIONS CONTAINING A MIXTURE OF A BICYCLICPOLYOXYMETHYLENEOXAZOLIDINE AND A 4-ISOTHIAZOLIN-3-ONE

This application is a continuation-in-part of application Ser. No. 894,264 filed Aug. 6, 1986 now abandoned.

BACKGROUND OF THE INVENTION

1. Field of the Invention

The present invention relates to inhibiting the growth of bacteria in various industrial environments. More particularly, the present invention relates to an improved microbiocidal composition and its method of use. Still more particularly, the present invention relates to a synergistic microbiocidal composition, and its method of use, the composition comprising a combination of a 4-isothiazolin-3-one and a bicyclic polyoxymethylene oxazolidine.

2. Description of the Prior Art

The presence of organic materials in the manufacture and/or use of various aqueous systems such as latices, adhesives, paints, coatings, mineral slurries and the like renders them susceptible to deterioration by virtue of exposure to bacteria and other microorganisms existing in the particular environment. It is, therefore, a conventional practice to seek to inhibit the microbial deterioration of such systems by incorporating therein any of various materials or combinations of materials that are characterized by having antibacterial activity.

Numerous materials have been found to possess such antibacterial activity among which are various polyoxymethyleneoxazolidines as disclosed in U.S. Pat. No. 4,135,945 and various 4-isothazoline-3-ones as disclosed in U.S. Pat. Nos. 4,174,643 and 3,929,561. In addition, U.S. Pat. Nos. 4,173,643, 3,231,509 and 3,929,561 disclose, respectively, synergistic combinations of quaternary ammonium salts with 4-isothiazolin-3-ones; quaternary ammonium salts with bis(halomethyl)sufones; and 4-isothiazolin-3-ones with bis(halomethyl)sulfones.

SUMMARY OF THE INVENTION

It is a principal object of this invention to provide an improved microbiocidal composition. It is a further object of this invention to provide an improved microbiocidal composition that is storage stable, and which is compatible with a variety of systems susceptible to biocidal degeneration thereby permitting its use without objectionable and/or unacceptable by-product odor, discoloration, thickening and the like. A further object of this invention is to provide an improved microbiocidal composition that is cost effective, i.e., performs effectively on the basis of its cost per unit weight and duration of its effectiveness on the treated system. Another object of this invention is to provide an improved method of inhibiting bacterial growth in a variety of systems used in industry and commerce.

DESCRIPTION OF THE PREFERRED EMBODIMENT

These various objects have been met in accordance with the present invention by a composition comprising (1) a 4-isothiazolin-3-one in combination with (2) a bicyclic polyoxymethyleneoxazolidine.

In accordance with the present invention, Component (1) of the composition, comprises a mixture of:

(a) 75% 5-chloro-2-methyl-4-isothiazolin-3-one, and (b) 25% 2-methyl-4-isothiazolin-3-one Component (2) of the composition of the present invention is represented by the formula:

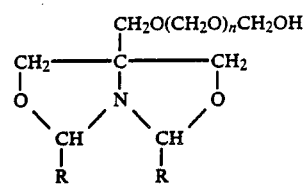

in which each R represents H, and alkyl of 1-6 carbons, phenyl, halophenyl or —$(CH_2O)_mCH_2OH$ in which m is 0-2 and n is 1-4.

The preferred bicyclic polyoxymethyleneoxazolidine for use in the composition of this invention comprises a mixture of:

(c) 35% 5-hydroxymethyl-1-aza-3,7-dioxabicyclo(3.3.0)-octane, (d) 49% 5-hydroxymethoxymethyl-1-aza-3,7-dioxabicyclo(3.3.0) octane, and (e) 16% 5-hydroxymethylpoly[oxymethylene($C_2$: 74%; $C_3$: 21%; $C_4$: 4%, $C_5$: 1%)]-1-aza-3,7-dioxabicyclo(3.3.0) octane.

In the practice of the invention, the composition may be used in a broad ratio of Component 1 to Component 2 ranging from about 1:50 to 50:1 parts by weight. Because of the cost factor, however, Component 2 will normally be used in excess, preferably in a ratio of 1:10 to 1:20 by weight. The composition can be employed in the form of a dilute aqueous or non-aqueous solution and can be added to the aqueous system to be treated in any conventional way in an amount effective to inhibit microorganism growth. Generally, the effective concentration will range from as little as 100 ppm to as much as 5000 ppm depending upon the nature of the system being treated. Usually, a concentration on the order of 500–2000 ppm will be found adequate.

In order to demonstrate the synergistic microbiocidal activity of the composition of this invention, the following example was conducted. All parts are by weight unless otherwise noted.

EXAMPLE

An unpreserved sample of styrene-butadiene-vinylidene chloride (SBVC) latex was analyzed for microbial content before being utilized for preservation evaluation according to the invention. It was determined that the latex sample was free of contamination.

The uncontaminated, unprotected SBVC latex was divided into 50 gr. aliquots and dosed with the microbiocide composition of this invention as reported in the following Table. Each of Components 1 and 2 was also separately tested as microbiocides while two aliquots remained untreated to serve as controls.

The challenged inoculum was a pooled suspension of microorganisms comprising the bacteria species Pseudomonas, Bacillus and Penicillium, that had been grown from contaminated latex material. All of the samples were challenged on a weekly basis for 4 weeks with 0.10 ml. of the pooled suspension containing at least $10^6$ organisms per ml. Following 72 hours of room temperature incubation, a 1 ml. quantity of each sample was transferred to 20 ml. of tryptic soy broth (TSB). The TSB tubes were incubated at room temperature for 24 hours and streaked onto TGE plates for growth bacteria. After 48 hours incubation at room temperature, the plates were read and graded according to the description in the Table.

The tested composition was the preferred composition referred to above in which Component 1 comprised elements (a) and (b) and Component 2 comprised elements (c), (d) and (e). Component (1) was obtained from Drew Chemical Corporation under the trademark Amerstat ® 251 as an aqueous solution containing 1.5% active ingredient. Component (2) was obtained from Nuodex, Inc. under the trademark Nuosept ® 95 as an aqueous solution containing 50% active ingredient. The composition of this invention was adjusted to an active ingredient content of 10% for testing. Component (1) was individually tested at its commercially available active ingredient content of 1.5% while Component (2) was individually tested at 20% total active ingredient. Results appear in the following Table.

TABLE

| Biocide | Ratio | PPM | Weekly Growth Rate* 1 | 2 | 3 | 4 |
|---|---|---|---|---|---|---|
| Components 1 and 2 | 1:10 | 500 | — | — | — | — |
| | | 1000 | — | — | — | — |
| | | 2000 | — | — | — | — |
| Components 1 and 2 | 1:15 | 500 | — | — | — | — |
| | | 1000 | — | — | — | — |
| | | 2000 | — | — | — | — |
| Components 1 and 2 | 1:20 | 500 | — | — | — | — |
| | | 1000 | — | — | — | — |
| | | 2000 | — | — | — | — |
| Component 1 | | 500 | +3 | +3 | +3 | +3 |
| | | 1000 | +2 | +2 | +2 | +3 |
| | | 2000 | — | +1 | +2 | +2 |
| Component 2 | | 500 | +1 | +1 | +1 | +2 |
| | | 1000 | — | +1 | +1 | +2 |
| | | 2000 | — | +1 | +1 | +1 |
| Control #1 | | | +2 | +4 | +4 | +4 |
| Control #2 | | | +4 | +4 | +4 | +4 |

*The rating system for microbial growth on streaked, prepoured agar plates is as follows:
Growth rate  Description

| Biocide | Ratio | PPM | Weekly Growth Rate* 1 | 2 | 3 | 4 |
|---|---|---|---|---|---|---|
| — | | | No growth; zero colonies | | | |
| +1 | | | Maximum of 15 total colonies with no more than 5 of these having diameters of ⅛ inch | | | |
| +2 | | | Sporadic growth on ½ total streaked area, remaining ½ area relatively clear; maximum of 20 total colonies with no more than 6 of these having diameters greater than ⅛ inch | | | |
| +3 | | | Dense growth on ⅜–¾ of streaked area; minor colonies too numerous to count; 20 or more major colonies having diameters of ⅛ inch or larger | | | |
| +4 | | | Uniform, dense growth over entire streaked area; colonies pinhead size or larger | | | |

Reference in the disclosure to details of specific embodiments is not intended to restrict the scope of the appended claims, which themselves recite those features regarded as essential to the invention.

What is claimed is:

1. A microbiocidal composition comprising a synergistic mixture the first component of which is a 4-isothiazolin-3-one comprising a mixture of (a) 75% 5-chloro-2-methyl-4-isothiazolin-3-one and (b) 25% 2-methyl-4-isothiazolin-3-one, and the second component of which is a bicyclic polyoxymethyleneoxazolidine comprising a mixture of (a) 35% 5-hydroxymethyl-1-aza-3,7 dioxabicyclo-(3.3.0)-octane, (b) 49% 5-hydroxymethylmethoxy-1-aza-3,7-dioxabicyclo(3.3.0)-octane, and (c) 16% 5-hydroxymethylpoly[oxymethylene($C_2$: 74%; $C_3$: 21%; $C_4$: 4%; $C_5$: 1%)]-1-aza-3,7-dioxabicyclo(3.3.0)-octane, said first and second components being in a ratio of 1:10–20 by weight.

2. A method for inhibiting the growth of bacteria in an aqueous system which comprises adding to said system an amount of a microbiocidal composition according to claim 1 effective to inhibit the growth of bacteria.

* * * * *